United States Patent
Duan et al.

(10) Patent No.: US 8,530,216 B2
(45) Date of Patent: Sep. 10, 2013

(54) POLYPEPTIDES HAVING ALPHA-AMYLASE ACTIVITY AND POLYNUCLEOTIDES ENCODING SAME

(75) Inventors: Junxin Duan, Beijing (CN); Zheng Liu, Beijing (CN); Ming Li, Beijing (CN); Jim Liu, Raleigh, NC (US); Guifang Wu, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 157 days.

(21) Appl. No.: 12/990,836

(22) PCT Filed: May 14, 2009

(86) PCT No.: PCT/US2009/043968
§ 371 (c)(1),
(2), (4) Date: Nov. 3, 2010

(87) PCT Pub. No.: WO2009/140504
PCT Pub. Date: Nov. 19, 2009

(65) Prior Publication Data
US 2011/0059492 A1    Mar. 10, 2011

Related U.S. Application Data

(60) Provisional application No. 61/053,685, filed on May 16, 2008.

(51) Int. Cl.
*C12N 9/30* (2006.01)
*C12N 15/00* (2006.01)
*C12N 5/00* (2006.01)
*C12P 19/00* (2006.01)
*C12P 19/12* (2006.01)
*C12P 19/02* (2006.01)
*C12P 7/06* (2006.01)
*C07H 21/04* (2006.01)

(52) U.S. Cl.
USPC ............ 435/203; 435/72; 435/100; 435/105; 435/161; 435/320.1; 435/325; 536/23.2

(58) Field of Classification Search
None
See application file for complete search history.

(56) References Cited

U.S. PATENT DOCUMENTS

| | | |
|---|---|---|
| 4,009,074 A | 2/1977 | Walon |
| 4,591,560 A | 5/1986 | Kainuma et al. |
| 4,727,026 A | 2/1988 | Sawada et al. |
| 2005/0048611 A1 | 3/2005 | Hoff et al. |

FOREIGN PATENT DOCUMENTS

| | | |
|---|---|---|
| EP | 0 171 218 A2 | 2/1986 |
| WO | WO 2006/066594 A2 | 6/2006 |
| WO | WO 2006/069290 A2 | 6/2006 |

*Primary Examiner* — Anand Desai
*Assistant Examiner* — Iqbal H Chowdhury
(74) *Attorney, Agent, or Firm* — Michael W. Krenicky

(57) ABSTRACT

The present invention relates to isolated polypeptides having alpha-amylase activity and isolated polynucleotides encoding the polypeptides. The invention also relates to nucleic acid constructs, vectors, and host cells comprising the polynucleotides as well as methods of producing and using the polypeptides.

15 Claims, 1 Drawing Sheet

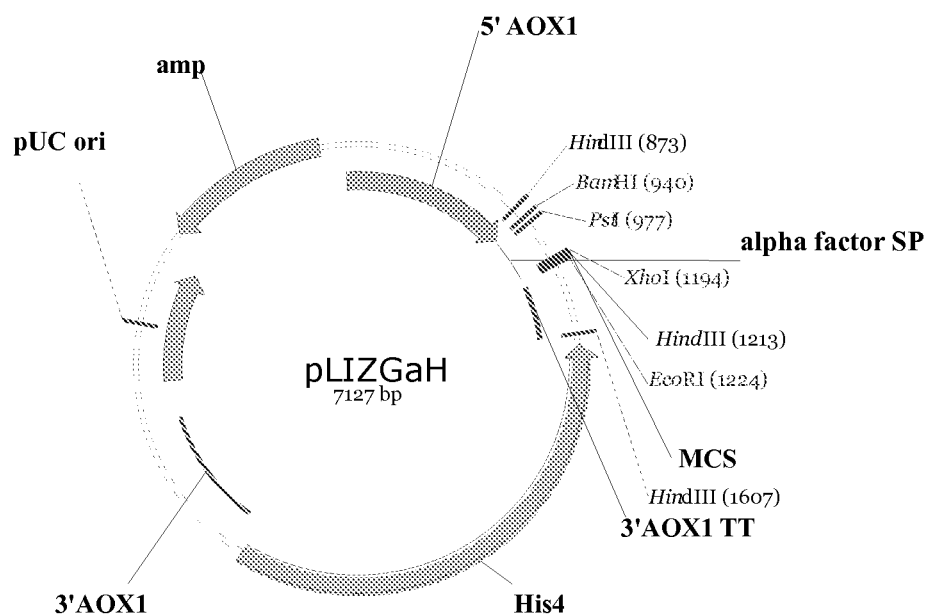

```
                        SEQUENCE LISTING

<160> NUMBER OF SEQ ID NOS: 9

<210> SEQ ID NO 1
<211> LENGTH: 1845
<212> TYPE: DNA
<213> ORGANISM: Subulispora species
<220> FEATURE:
<221> NAME/KEY: misc_feature
<222> LOCATION: (1)..(1845)
<223> OTHER INFORMATION: Gene encoding SEQ ID NO:2

<400> SEQUENCE: 1
atgcgggcga acggcatttt aatccccggc ctctgggccg ccgccgctca ggccttgact      60
cccgccgaat ggggaagcca gagcatctac caggttctga ccgatcgctt cgcactgact     120
gacgggtcca cgacggcctc ctgcgacctg aatacttact gtggcggcac ttggctaggt     180
atccagaacc accttgacta catccaaggc atgggcttta ctgctatctg gatctctccc     240
atcgtgacca atatcgcagg tgactctgtt gatggggact cctaccatgg ctactgggct     300
caggacatca cgacggtgaa ctccgccttc gggacggagc aggacctcat taatctctcg     360
gcagccctgc acgagagggg catgtatcta atggtcgacg tggtgaacaa ccacatggga     420
tacctcggct gcggaacttg tgtcgactac agcgagtaca cgcctttcaa cgaagagtcg     480
tactaccacc cgtactgccc aaccgactac agcaacttga cctccattca ggtgtgctgg     540
gaaggtgaca acattgtcag tcttcctgac ctcaggaccg aggactcgga tgttcgtagc     600
atgtggtacg actggatcac gccgctcgtg gccaagtact ccatcgacgg gctccgaatg     660
gacagcgccg aacatgtaga gaagtccttc tggccaggat gggtatctgc atcgggagta     720
tacaacgtgg gagaggtcga tgaaggggat ccaaccatct ttcccgactg gctgaattac     780
atcgatggga ccttgaacta tccagcctat tactggatca cgcaagcctt ccagtcgaca     840
tcgggttcaa tcagcaacct ggttaccggg gtcaaccagc tgaaggcctc aatgaaaacc     900
```

-continued

```
agcacattcg gatcgttcct cgagaaccac gatcagcctc gtttcccatc cctgactagt    960
gatacggatt tggcaaagaa tgcgattgct tttgctatgc ttgctgacgg cgtccctatc   1020
gtatactacg gccaagagca gggctactct ggtggcggcg tgcccaatga tcgggagccc   1080
ctctggacct ccgggtattc tacgacgtcc gcaggataca ccttcatcaa gaccatcaac   1140
gcggttcgcc acctggccgt cacccaggac accgcatacg ttgcttacca agcctaccca   1200
atctactcgg actcgcgcgt gatcgccatg aagaagagca cgtcctcgc cgtcttcagc    1260 aacatcggct ccagcggcag cggctactcc atcacactgc cggccggcgc gttcgcggcg   1320
agccaggcgc tcactgatgc ggtcagctgc cagacttaca cggctgacgc gagtggcggc   1380
ctcaccttca cgttcggaca ggcgccgtcg gtgttctacg cgacggccag cctggccggc   1440
agcggattgt gcggtacgac ggggacgggg ggcagcactg gcactactac cgcttccgag   1500
accggaggat catcgccaac ctcgacagca tgcgcgtccg tccccgtaac ttttaacgag   1560
aaggttacga ccgtcgtcgg ggagacgatc aagatatccg gcagcgtggc cgccctcggc   1620
gactgggcca cgggcagcgc ggtggccctg agcgccgcga gctacacgtc agcaacccg    1680 cagtgggacg tgaccatcag ctttgcgccg gcaccgtga tcgagtacaa gtacatcaac    1740
gtggcgagca gcggggccgt gacctgggag ccgacccga accacacgta cacggtcccg    1800
gcgtcctgcg ccacggccgc cgtcgtgtct gacacgtggc agacg                   1845
```

<210> SEQ ID NO 2
<211> LENGTH: 615
<212> TYPE: PRT
<213> ORGANISM: Subulispora species.
<220> FEATURE:
<221> NAME/KEY: SIGNAL
<222> LOCATION: (1)..(18)

<400> SEQUENCE: 2

```
Met Arg Ala Asn Gly Ile Leu Ile Pro Gly Leu Trp Ala Ala Ala
1               5                   10                  15

Gln Ala Leu Thr Pro Ala Glu Trp Gly Ser Gln Ser Ile Tyr Gln Val
                20                  25                  30

Leu Thr Asp Arg Phe Ala Leu Thr Asp Gly Ser Thr Thr Ala Ser Cys
            35                  40                  45

Asp Leu Asn Thr Tyr Cys Gly Gly Thr Trp Leu Gly Ile Gln Asn His
        50                  55                  60

Leu Asp Tyr Ile Gln Gly Met Gly Phe Thr Ala Ile Trp Ile Ser Pro
65                  70                  75                  80

Ile Val Thr Asn Ile Ala Gly Asp Ser Val Asp Gly Asp Ser Tyr His
                85                  90                  95

Gly Tyr Trp Ala Gln Asp Ile Thr Val Asn Ser Ala Phe Gly Thr
            100                 105                 110

Glu Gln Asp Leu Ile Asn Leu Ser Ala Ala Leu His Glu Arg Gly Met
        115                 120                 125

Tyr Leu Met Val Asp Val Val Asn Asn His Met Gly Tyr Leu Gly Cys
    130                 135                 140

Gly Thr Cys Val Asp Tyr Ser Glu Tyr Thr Pro Phe Asn Glu Glu Ser
145                 150                 155                 160

Tyr Tyr His Pro Tyr Cys Pro Asp Tyr Ser Asn Leu Thr Ser Ile
                165                 170                 175

Gln Val Cys Trp Glu Gly Asp Asn Ile Val Ser Leu Pro Asp Leu Arg
            180                 185                 190

Thr Glu Asp Ser Asp Val Arg Ser Met Trp Tyr Asp Trp Ile Thr Pro
```

-continued

```
                195                 200                 205
Leu Val Ala Lys Tyr Ser Ile Asp Gly Leu Arg Met Asp Ser Ala Glu
210                 215                 220
His Val Glu Lys Ser Phe Trp Pro Gly Trp Val Ser Ala Ser Gly Val
225                 230                 235                 240
Tyr Asn Val Gly Glu Val Asp Glu Gly Asp Pro Thr Ile Phe Pro Asp
                245                 250                 255
Trp Leu Asn Tyr Ile Asp Gly Thr Leu Asn Tyr Pro Ala Tyr Tyr Trp
            260                 265                 270
Ile Thr Gln Ala Phe Gln Ser Thr Ser Gly Ser Ile Ser Asn Leu Val
            275                 280                 285
Thr Gly Val Asn Gln Leu Lys Ala Ser Met Lys Thr Ser Thr Phe Gly
290                 295                 300
Ser Phe Leu Glu Asn His Asp Gln Pro Arg Phe Pro Ser Leu Thr Ser
305                 310                 315                 320
Asp Thr Asp Leu Ala Lys Asn Ala Ile Ala Phe Ala Met Leu Ala Asp
                325                 330                 335
Gly Val Pro Ile Val Tyr Tyr Gly Gln Glu Gln Gly Tyr Ser Gly Gly
            340                 345                 350
Gly Val Pro Asn Asp Arg Glu Pro Leu Trp Thr Ser Gly Tyr Ser Thr
            355                 360                 365
Thr Ser Ala Gly Tyr Thr Phe Ile Lys Thr Ile Asn Ala Val Arg His
370                 375                 380
Leu Ala Val Thr Gln Asp Thr Ala Tyr Val Ala Tyr Gln Ala Tyr Pro
385                 390                 395                 400
Ile Tyr Ser Asp Ser Arg Val Ile Ala Met Lys Lys Ser Ser Val Leu
                405                 410                 415
Ala Val Phe Ser Asn Ile Gly Ser Ser Gly Ser Gly Tyr Ser Ile Thr
            420                 425                 430
Leu Pro Ala Gly Ala Phe Ala Ala Ser Gln Ala Leu Thr Asp Ala Val
            435                 440                 445
Ser Cys Gln Thr Tyr Thr Ala Asp Ala Ser Gly Gly Leu Thr Phe Thr
450                 455                 460
Phe Gly Gln Ala Pro Ser Val Phe Tyr Ala Thr Ala Ser Leu Ala Gly
465                 470                 475                 480
Ser Gly Leu Cys Gly Thr Thr Gly Thr Gly Ser Thr Gly Thr Thr
                485                 490                 495
Thr Ala Ser Glu Thr Gly Gly Ser Ser Pro Thr Ser Thr Ala Cys Ala
            500                 505                 510
Ser Val Pro Val Thr Phe Asn Glu Lys Val Thr Thr Val Val Gly Glu
            515                 520                 525
Thr Ile Lys Ile Ser Gly Ser Val Ala Ala Leu Gly Asp Trp Ala Thr
530                 535                 540
Gly Ser Ala Val Ala Leu Ser Ala Ser Tyr Thr Ser Ser Asn Pro
545                 550                 555                 560
Gln Trp Asp Val Thr Ile Ser Phe Ala Pro Gly Thr Val Ile Glu Tyr
                565                 570                 575
Lys Tyr Ile Asn Val Ala Ser Ser Gly Ala Val Thr Trp Glu Ala Asp
            580                 585                 590
Pro Asn His Thr Tyr Thr Val Pro Ala Ser Cys Ala Thr Ala Ala Val
            595                 600                 605
Val Ser Asp Thr Trp Gln Thr
610                 615
```

```
<210> SEQ ID NO 3
<211> LENGTH: 18
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: w= g or c
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: y= t or c
<220> FEATURE:
<221> NAME/KEY: misc_feature
<222> LOCATION: (12)..(12)
<223> OTHER INFORMATION: n is a, c, g, or t

<400> SEQUENCE: 3
gwntaccayg gntactgg                                                   18

<210> SEQ ID NO 4
<211> LENGTH: 18
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (15)..(15)
<223> OTHER INFORMATION: r= t or g
<220> FEATURE:
<221> NAME/KEY: misc_feature
<222> LOCATION: (16)..(16)
<223> OTHER INFORMATION: d= a or g

<400> SEQUENCE: 4
gtcgtggttc tcgardaa                                                   18

<210> SEQ ID NO 5
<211> LENGTH: 22
<212> TYPE: DNA
<213> ORGANISM: Artificial sequence
<220> FEATURE:
<223> OTHER INFORMATION: Synthetic construct

<400> SEQUENCE: 5
tggaggtcaa gttgctgtag tc                                              22

<210> SEQ ID NO 6
<211> LENGTH: 25
<212> TYPE: DNA
<213> ORGANISM: Artificial sequence
<220> FEATURE:
<223> OTHER INFORMATION: Synthetic construct

<400> SEQUENCE: 6
gcaactgtag acgattcgga ctgta                                           25

<210> SEQ ID NO 7
<211> LENGTH: 21
<212> TYPE: DNA
<213> ORGANISM: Artificial sequence
<220> FEATURE:
<223> OTHER INFORMATION: Synthetic construct
```

```
<400> SEQUENCE: 7
atgcgggcga acggcatttt a                                                    21

<210> SEQ ID NO 8
<211> LENGTH: 36
<212> TYPE: DNA
<213> ORGANISM: Artificial sequence
<220> FEATURE:
<223> OTHER INFORMATION: Synthetic construct

<400> SEQUENCE: 8
attattcgaa ggatccacca tgcgggcgaa cggcat                                    36

<210> SEQ ID NO 9
<211> LENGTH: 38
<212> TYPE: DNA
<213> ORGANISM: Artificial sequence
<220> FEATURE:
<223> OTHER INFORMATION: Synthetic construct

<400> SEQUENCE: 9
gatggtgatg gaattccgtc tgccacgtgt cagacacg                                  38
```

POLYPEPTIDES HAVING ALPHA-AMYLASE ACTIVITY AND POLYNUCLEOTIDES ENCODING SAME

CROSS-REFERENCE TO RELATED APPLICATIONS

This application is a 35 U.S.C. 371 national application of PCT/US2009/043968 filed May 14, 2009, which claims priority or the benefit under 35 U.S.C. 119 of U.S. provisional application No. 61/053,685 filed May 16, 2008 the contents of which are fully incorporated herein by reference.

REFERENCE TO A SEQUENCE LISTING

This application contains a Sequence Listing in computer readable form, which is incorporated herein by reference.

REFERENCE TO A DEPOSIT OF BIOLOGICAL MATERIAL

This application contains a reference to a deposit of biological material, which deposit is incorporated herein by reference.

BACKGROUND OF THE INVENTION

1. Field of the Invention

The present invention relates to isolated polypeptides having alpha-amylase activity and isolated polynucleotides encoding the polypeptides. The invention also relates to nucleic acid constructs, vectors, and host cells comprising the polynucleotides as well as methods of producing and using the polypeptides.

2. Description of the Related Art

Alpha-amylases (alpha-1,4-glucan-4-glucanohydrolases, EC. 3.2.1.1) constitute a group of enzymes which catalyze hydrolysis of starch and other linear and branched 1,4-glucosidic oligo- and polysaccharides.

For a number of years alpha-amylase enzymes have been used for a variety of different purposes, the most important of which are starch liquefaction, textile desizing, starch modification in the paper and pulp industry, and for brewing, ethanol production and baking.

In the case of converting starch into a soluble starch hydrolysate, the starch is depolymerized. The conventional depolymerization process consists of a gelatinization step and two consecutive process steps, namely a liquefaction process and a saccharification process.

Granular starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typical industrial process, the starch has to be thinned or "liquefied" so that it can be handled. This reduction in viscosity is today mostly obtained by enzymatic degradation. During the liquefaction step, the long-chained starch is degraded into smaller branched and linear units (maltodextrins) by an alpha-amylase. The liquefaction process is typically carried out at about 105-110° C. for about 5 to 10 minutes followed by about 1-2 hours at about 95° C. The temperature is then lowered to 60° C., a glucoamylase (also known as GA or AMG) or a beta-amylase and optionally a debranching enzyme, such as an isoamylase or a pullulanase are added, and the saccharification process proceeds for about 24 to 72 hours. After saccharification process, the sugar can be converted to ethonal by a fermentation organism, preferably yeast.

It will be apparent from the above discussion that the conventional starch conversion process is very energy consuming due to the different requirements in terms of temperature during the various steps. Processes of conversion of starch without having to gelatinize the starch exist. Such "raw starch" processes are described in U.S. Pat. Nos. 4,591,560, 4,727,026 and 4,009,074, EP Patent No. 0171218 and Danish patent application PA 2003 00949. A polypeptide from *Subulispora procurvata* having alpha-amylase activity is disclosed in SEQ ID NO: 169 of WO 2006/069290.

It would be advantageous to provide alternative alpha-amylases having different properties than the previously known alpha-amylases, to be used in the starch conversion process so that the overall processes can be combined in one step.

SUMMARY OF THE INVENTION

The present invention relates to isolated polypeptides having alpha-amylase activity selected from the group consisting of:

(a) a polypeptide comprising an amino acid sequence having at least 90% identity to the mature polypeptide of SEQ ID NO: 2;

(b) a polypeptide encoded by a polynucleotide that hybridizes under at least medium stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii);

(c) a polypeptide encoded by a polynucleotide comprising a nucleotide sequence having at least 90% identity to the mature polypeptide coding sequence of SEQ ID NO: 1; and (d) a variant comprising a substitution, deletion, and/or insertion of one or more (several) amino acids of the mature polypeptide of SEQ ID NO: 2.

The present invention also relates to isolated polynucleotides encoding polypeptides having alpha-amylase activity, selected from the group consisting of:

(a) a polynucleotide encoding a polypeptide comprising an amino acid sequence having at least 90% identity to the mature polypeptide of SEQ ID NO: 2;

(b) a polynucleotide that hybridizes under at least medium stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii);

(c) a polynucleotide comprising a nucleotide sequence having at least 90% identity to the mature polypeptide coding sequence of SEQ ID NO: 1; and (d) a polynucleotide encoding a variant comprising a substitution, deletion, and/or insertion of one or more amino acids of the mature polypeptide of SEQ ID NO: 2.

The present invention also relates to nucleic acid constructs, recombinant expression vectors, recombinant host cells comprising the polynucleotides, and methods of producing a polypeptide having alpha-amylase activity.

The present invention also relates to methods of inhibiting the expression of a polypeptide in a cell, comprising administering to the cell or expressing in the cell a double-stranded RNA (dsRNA) molecule, wherein the dsRNA comprises a subsequence of a polynucleotide of the present invention. The present also relates to such a double-stranded inhibitory RNA (dsRNA) molecule, wherein optionally the dsRNA is a siRNA or a miRNA molecule.

The present invention also relates to methods for degrading material comprising starch.

The present invention also relates to plants comprising an isolated polynucleotide encoding such a polypeptide having alpha-amylase activity.

The present invention also relates to methods of producing such a polypeptide having alpha-amylase, comprising: (a) cultivating a transgenic plant or a plant cell comprising a polynucleotide encoding such a polypeptide having alpha-amylase activity under conditions conducive for production of the polypeptide; and (b) recovering the polypeptide.

The present invention further relates to nucleic acid constructs comprising a gene encoding a protein, wherein the gene is operably linked to a nucleotide sequence encoding a signal peptide comprising or consisting of amino acids 1 to 18 of SEQ ID NO: 2, wherein the gene is foreign to the nucleotide sequence.

BRIEF DESCRIPTION OF THE FIGURES

FIG. 1 shows the restriction map of pLIZGaH.

DEFINITIONS

Alpha-amylase activity: The term "alpha-amylase activity" is defined herein as a 1,4-glucan-4-glucanohydrolases (EC. 3.2.1.1) activity which catalyzes the hydrolysis of starch and other linear and branched 1,4-glucosidic oligo- and polysaccharides. Alpha-amylase activity is determined according to the procedure described in the Examples.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the alpha-amylase activity of the mature polypeptide of SEQ ID NO: 2.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide having alpha-amylase activity that is in its final form following translation and any post-translational modifications, such as N-terminal processing, C-terminal truncation, glycosylation, phosphorylation, etc. In a preferred aspect, the mature polypeptide is amino acids 19 to 615 of SEQ ID NO: 2 based on the SignalP program that predicts amino acids 1 to 18 of SEQ ID NO: 2 are a signal peptide.

Mature polypeptide coding sequence: The term "mature polypeptide coding sequence" is defined herein as a nucleotide sequence that encodes a mature polypeptide having alpha-amylase activity. In a preferred aspect, the mature polypeptide coding sequence is nucleotides 55 to 1845 of SEQ ID NO: 1 based on the SignalP program that predicts nucleotides 1 to 54 of SEQ ID NO: 1 encode a signal peptide.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein that gives an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Subulispora* sp. alpha-amylase of SEQ ID NO: 2 or the mature polypeptide thereof.

Polypeptide fragment: The term "polypeptide fragment" is defined herein as a polypeptide having one or more (several) amino acids deleted from the amino and/or carboxyl terminus of the mature polypeptide of SEQ ID NO: 2; or a homologous sequence thereof; wherein the fragment has alpha-amylase activity. In a preferred aspect, a fragment contains at least 500 amino acid residues, more preferably at least 550 amino acid residues, most preferably at least 600 amino acids of SEQ ID NO: 2, or a homologous sequence thereof.

Subsequence: The term "subsequence" is defined herein as a nucleotide sequence having one or more (several) nucleotides deleted from the 5' and/or 3' end of the mature polypeptide coding sequence of SEQ ID NO: 1; or a homologous sequence thereof; wherein the subsequence encodes a polypeptide fragment having alpha-amylase activity. In a preferred aspect, a subsequence contains at least 1500 nucleotides, more preferably at least 1650 nucleotides, and most preferably at least 1800 nucleotides of the mature polypeptide coding sequence of SEQ ID NO: 1 or a homologous sequence thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: The term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals.

The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: The term "artificial variant" means a polypeptide having alpha-amylase activity produced by an organism expressing a modified polynucleotide sequence of the mature polypeptide coding sequence of SEQ ID NO: 1; or a homologous sequence thereof. The modified nucleotide sequence is obtained through human intervention by modification of the polynucleotide sequence disclosed in SEQ ID NO: 1; or a homologous sequence thereof.

DETAILED DESCRIPTION OF THE INVENTION

Polypeptides Having Alpha-Amylase Activity

In a first aspect, the present invention relates to isolated polypeptides comprising an amino acid sequence having a degree of identity to the mature polypeptide of SEQ ID NO: 2 of at least 90%, preferably at least 93%, more preferably at least 95%, more preferably at least 96%, and even more preferably at least 97%, at least 98%, or at least 99%, which have alpha-amylase activity (hereinafter "homologous polypeptides"). In a preferred aspect, the homologous polypeptides have an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 2.

A polypeptide of the present invention preferably comprises the amino acid sequence of SEQ ID NO: 2 or an allelic variant thereof; or a fragment thereof having alpha-amylase activity. In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide comprises amino acids 19 to 615 of SEQ ID NO: 2, or an allelic variant thereof; or a fragment thereof having alpha-amylase activity. In another preferred aspect, the polypeptide comprises amino acids 19 to 615 of SEQ ID NO: 2. In another preferred aspect, the polypeptide consists of the amino acid sequence of SEQ ID NO: 2 or an allelic variant thereof; or a fragment thereof having alpha-amylase activity. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 19 to 615 of SEQ ID NO: 2 or an allelic variant thereof; or a fragment thereof having alpha-amylase activity. In another preferred aspect, the polypeptide consists of amino acids 19 to 615 of SEQ ID NO: 2.

In a second aspect, the present invention relates to isolated polypeptides having alpha-amylase activity that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the cDNA sequence contained in the mature polypeptide coding sequence of SEQ ID NO: 1, (iii) a subsequence of (i) or (ii), or (iv) a full-length complementary strand of (i), (ii), or (iii) (J. Sambrook, E. F. Fritsch, and T. Maniatis, 1989, *Molecular Cloning, A Laboratory Manual*, 2d edition, Cold Spring Harbor, N.Y.). A subsequence of the mature polypeptide coding sequence of SEQ ID NO: 1 contains at least 100 contiguous nucleotides or preferably at least 200 contiguous nucleotides. Moreover, the subsequence may encode a polypeptide fragment having alpha-amylase activity. In a preferred aspect, the complementary strand is the full-length complementary strand of the mature polypeptide coding sequence of SEQ ID NO: 1.

The nucleotide sequence of SEQ ID NO: 1 or a subsequence thereof; as well as the amino acid sequence of SEQ ID NO: 2 or a fragment thereof; may be used to design nucleic acid probes to identify and clone DNA encoding polypeptides having alpha-amylase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may, therefore, be screened for DNA that hybridizes with the probes described above and encodes a polypeptide having alpha-amylase activity. Genomic or other DNA from such other strains may be separated by agarose or polyacrylamide gel electrophoresis, or other separation techniques.

DNA from the libraries or the separated DNA may be transferred to and immobilized on nitrocellulose or other suitable carrier material. In order to identify a clone or DNA that is homologous with SEQ ID NO: 1; or a subsequence thereof; the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1; the cDNA sequence contained in the mature polypeptide coding sequence of SEQ ID NO: 1; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 55 to 1845 of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pGEM-T which is contained in *E. coli* DSM19686, wherein the polynucleotide sequence thereof encodes a polypeptide having alpha-amylase activity. In another preferred aspect, the nucleic acid probe is the mature polypeptide coding region contained in plasmid pGEM-T which is contained in *E. coli* DSM19686.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$, using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having alpha-amylase activity encoded by polynucleotides comprising or consisting of nucleotide sequences that have a degree of identity to the mature polypeptide coding sequence of SEQ ID NO: 1 of at least 90%, more preferably at least 93%, most preferably at least 95%, and even most preferably 96%, 97%, 98%, or 99%, which encode an active polypeptide. See polynucleotide section herein.

In a fourth aspect, the present invention relates to artificial variants comprising a substitution, deletion, and/or insertion of one or more (or several) amino acids of the mature polypeptide of SEQ ID NO: 2; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., alpha-amylase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2, such as amino acids 19 to 615 of SEQ ID NO: 2, is 10, preferably 9, more preferably 8, more preferably 7, more preferably at most 6, more preferably 5, more preferably 4, even more preferably 3, most preferably 2, and even most preferably 1.

Sources of Polypeptides Having Alpha-amylase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having alpha-amylase activity of the present invention may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus*, or *Oceanobacillus* polypeptide having alpha-amylase activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having alpha-amylase activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having alpha-amylase activity.

In another preferred aspect, the polypeptide is a *Streptococcus equisimilis, Streptococcus pyogenes, Streptococcus uberis*, or *Streptococcus equi* subsp. *Zooepidemicus* polypeptide having alpha-amylase activity.

In another preferred aspect, the polypeptide is a *Streptomyces achromogenes, Streptomyces avermitilis, Streptomyces coelicolor, Streptomyces griseus*, or *Streptomyces lividans* polypeptide having alpha-amylase activity.

A polypeptide having alpha-amylase activity of the present invention may also be a fungal polypeptide, and more preferably a yeast polypeptide such as a *Candida, Kluyveromyces, Pichia, Saccharomyces, Schizosaccharomyces*, or *Yarrowia* polypeptide having alpha-amylase activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having alpha-amylase activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having alpha-amylase activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei*, or *Trichoderma viride* polypeptide having alpha-amylase activity.

In a more preferred aspect, the polypeptide is a *Subulispora* sp. polypeptide having alpha-amylase activity. In a most preferred aspect, the polypeptide having alpha-amylase activity, e.g., the polypeptide comprising the mature polypeptide of SEQ ID NO: 2.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having alpha-amylase activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-76; Svetina et al., 2000, *J. Biotechnol.* 76: 245-251; Rasmussen-Wilson et al., 1997, *Appl. Environ. Microbiol.* 63: 3488-3493;

Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode polypeptides having alpha-amylase activity of the present invention.

In a preferred aspect, the nucleotide sequence comprises or consists of SEQ ID NO: 1. In another more preferred aspect, the nucleotide sequence comprises or consists of the sequence contained in plasmid pGEM-T which is contained in *E. coli* DSM19686. In another preferred aspect, the nucleotide sequence comprises or consists of the mature polypeptide coding sequence of SEQ ID NO: 1. In another preferred aspect, the nucleotide sequence comprises or consists of nucleotides 55 to 1845 of SEQ ID NO: 1. In another more preferred aspect, the nucleotide sequence comprises or consists of the mature polypeptide coding sequence contained in plasmid pGEM-T which is contained in *E. coli* DSM19686. The present invention also encompasses nucleotide sequences that encode polypeptides comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 that encodes fragments of SEQ ID NO: 2 that have alpha-amylase activity.

The present invention also relates to mutant polynucleotides comprising or consisting of at least one mutation in the mature polypeptide coding sequence of SEQ ID NO: 1, in which the mutant nucleotide sequence encodes the mature polypeptide of SEQ ID NO: 2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Subulispora*, or another or related organism and thus, for example, may be an allelic or species variant of the polypeptide encoding region of the nucleotide sequence.

The present invention also relates to isolated polynucleotides comprising or consisting of nucleotide sequences that have a degree of identity to the mature polypeptide coding sequence of SEQ ID NO: 1 of at least 90%, more preferably at least 95%, and even most preferably at least 96%, at least 97%, at least 98%, or at least 99% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 1, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide.

Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for alpha-amylase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii); or allelic variants and subsequences thereof (Sambrook et al., 1989, supra), as defined herein. In a preferred aspect, the complementary strand is the full-length complementary strand of the mature polypeptide coding sequence of SEQ ID NO: 1.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii); and (b) isolating the hybridizing polynucleotide, which encodes a polypeptide having alpha-amylase activity. In a preferred aspect, the complementary strand is the full-length complementary strand of the mature polypeptide coding sequence of SEQ ID NO: 1.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (VIIIa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In a preferred aspect, the signal peptide comprises or consists of amino acids 1 to 18 of SEQ ID NO: 2. In another preferred aspect, the signal peptide coding sequence comprises or consists of nucleotides 1 to 54 of SEQ ID NO: 1.

The control sequence may also be a propeptide coding sequence that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (or several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Subulispora*. In a more preferred aspect, the cell is *Subulispora* sp.

The present invention also relates to methods of producing a polypeptide of the present invention, comprising: (a) cultivating a recombinant host cell, as described herein, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO: 1, wherein the mutant nucleotide sequence encodes a polypeptide that comprises or consists of the mature polypeptide of SEQ ID NO: 2; and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to plants, e.g., a transgenic plant, plant part, or plant cell, comprising an isolated polynucleotide encoding a polypeptide having alpha-amylase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more (several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequence is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-

1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods of producing a polypeptide of the present invention comprising: (a) cultivating a transgenic plant or a plant cell comprising a polynucleotide encoding the polypeptide having alpha-amylase activity of the present invention under conditions conducive for production of the polypeptide; and (b) recovering the polypeptide.

Compositions

The present invention also relates to compositions comprising a polypeptide of the present invention.

The composition may further comprise an enzyme selected from the group comprising of: a fungal alpha-amylase (EC 3.2.1.1), a beta-amylase (E.C. 3.2.1.2), a glucoamylase (E.C.3.2.1.3) and a pullulanases (E.C. 3.2.1.41). The glucoamylase may preferably be derived from a strain of *Aspergillus* sp., such as *Aspergillus niger*, or from a strain of *Talaromyces* sp. and in particular derived from *Talaromyces leycettanus* such as the glucoamylase disclosed in U.S. Pat. No. Re. 32,153, *Talaromyces duponti* and/or *Talaromyces thermopiles* such as the glucoamylases disclosed in U.S. Pat. No. 4,587,215 and more preferably derived from *Talaromyces emersonii*. Most preferably the glucoamylase is derived from *Talaromyces emersonii* strain CBS 793.97 and/or having the sequence disclosed as SEQ ID NO: 7 in WO 99/28448. Further preferred is a glucoamylase which has an amino acid sequence having at least 50%, at least 60%, at least 70%, at least 80%, at least 90% or even at least 95% homology to the aforementioned amino acid sequence. A commercial *Talaromyces* glucoamylase preparation is supplied by Novozymes A/S as Spirizyme Fuel.

Also preferred for a composition comprising the polypeptide of the present invention and a glucoamylase are polypeptides having glucoamylase activity which are derived from a strain of the genus *Trametes*, preferably *Trametes cingulata*. Further preferred is polypeptide having glucoamylase activity and having at least 50%, at least 60%, at least 70%, at least 80%, at least 90% or even at least 95% homology with amino acids for mature polypeptide of SEQ ID NO: 2 in WO 2006/069289.

Also preferred for a composition comprising the polypeptide of the present invention and a glucoamylase are polypeptides having glucoamylase activity which are derived from a strain of the genus *Pachykytospora*, preferably *Pachykytospora papyracea* or the *E. coli* strain deposited at DSMZ and given the no. DSM 17105. Further preferred are polypeptides having glucoamylase activity and having at least 50%, at least 60%, at least 70%, at least 80%, at least 90% or even at least 95% homology with amino acids for mature polypeptide of SEQ ID NO: 5 in WO 2006/069289.

The composition described above may be used for liquefying and/or saccharifying a gelatinized or a granular starch, as well as a partly gelatinized starch. A partly gelatinized starch is a starch which to some extent is gelatinized, i.e., wherein part of the starch has irreversibly swelled and gelatinized and part of the starch is still present in a granular state.

The composition described above may preferably comprise acid alpha-amylase present in an amount of 0.01 to 10 AFAU/g DS, preferably 0.1 to 5 AFAU/g DS, more preferably 0.5 to 3 AFAU/AGU, and most preferably 0.3 to 2 AFAU/g DS. The dosage of the polypeptide composition of the invention and other conditions under which the composition is used may be determined on the basis of methods known in the art.

The polypeptide compositions may be prepared in accordance with methods known in the art and may be in the form of a liquid or a dry composition. For instance, the polypeptide composition may be in the form of granulate or a microgranulate. The polypeptide to be included in the composition may be stabilized in accordance with methods known in the art.

Uses

The present invention is also directed to methods for using the polypeptides having alpha-amylase activity, or compositions thereof.

The polypeptide or the composition of the present invention may be used in starch conversion, starch to sugar conversion and ethonal production etc, e.g., in liquefying and/or saccharifying a gelatinized starch or a granular starch, as well as a partly gelatinized starch. A partly gelatinized starch is a starch which to some extent is gelatinized, i.e., wherein part of the starch has irreversibly swelled and gelatinized and part of the starch is still present in a granular state. It can be used in a process for liquefying starch, wherein a gelatinized or granular starch substrate is treated in aqueous medium with the enzyme. The polypeptide or the composition of the present invention may also be used in a process for saccharification of a liquefied starch substrate. A preferred use is in a fermentation process wherein a starch substrate is liquefied and/or saccharified in the presence of the polypeptide or the composition of the present invention to produce glucose and/or maltose suitable for conversion into a fermentation product by a fermenting organism, preferably a yeast. Such fermentation processes include a process for producing ethanol for fuel or drinking ethanol (portable alcohol), a process for producing a beverage, a process for producing desired organic compounds, such as citric acid, itaconic acid, lactic acid, gluconic acid, sodium gluconate, calcium gluconate, potassium gluconate, glucono delta lactone, or sodium erythorbate; ketones; amino acids, such as glutamic acid (sodium monoglutaminate), but also more complex compounds such as antibiotics, such as penicillin, tetracyclin; enzymes; vitamins, such as riboflavin, B12, beta-carotene; hormones, which are difficult to produce synthetically.

Furthermore, due to the superior hydrolysis activity of the polypeptide of the first aspect the need for glucoamylase during the saccharification step is greatly reduced. The glucoamylase may preferably be derived from a strain within *Aspergillus* sp., *Talaromyces* sp., *Pachykytospora* sp. or *Trametes* sp., more preferably from *Aspergillus niger, Talaromyces emersonii, Trametes cingulata* or *Pachykytospora papyracea*.

In a preferred embodiment, the polypeptide of the present invention is used in a process comprising fermentation to produce a fermentation product, e.g., ethanol. Such a process for producing ethanol from starch-containing material by fermentation comprises: (i) liquefying said starch-containing material with a polypeptide with alpha-amylase activity of the present invention; (ii) saccharifying the liquefied mash obtained; (iii) fermenting the material obtained in step (ii) in the presence of a fermenting organism. Optionally the process further comprises recovery of the ethanol. The saccharification and fermentation may be carried out as a simultaneous saccharification and fermentation process (SSF process).

In another preferred embodiment, the polypeptide of the present invention is used in a process comprising fermentation to produce a fermentation product, e.g., ethanol, from an ungelatinized ("raw") starch. Such a process for producing ethanol from ungelatinized starch-containing material by fermentation comprises: (i) contacting the ungelatinized starch with a polypeptide with alpha-amylase activity of the present invention to degrade the ungelatinized starch; (ii) saccharifying the mash obtained; (iii) fermenting the material obtained in step (ii) in the presence of a fermenting organism. Optionally the process further comprises recovery of the ethanol. The saccharification and fermentation may be carried out as a simultaneous saccharification and fermentation process (SSF process).

The polypeptide or the composition of the present invention may be used in a process of desizing a sized fabric during manufacture to facilitate the removal of starch-containing size which has served as a protective coating on yarns during weaving.

After the desizing step it is often desirable to include a demineralization step in order to remove metal ions, such as $Mn^{2+}$, $Fe^{2+}/Fe^{3+}$, $Cu^{2+}$ etc., which—if present on the fabric— may result in an uneven bleaching in a later process step or might even make pin-holes in the bleached fabric. Demineralization is typically accomplished by acid precipitation and typically involves addition of acids such as acetic acid or sulphuric acid.

In a preferred embodiment, when carrying out the desizing process using the polypeptide of the present invention, no demineralization is needed. Fabric may be desized and demineralised simultaneously in the same aqueous treating solution or subsequently in the same or two separate treating solutions. In a preferred embodiment the desizing and demineralization are carried out simultaneously in the same treating solution. The process of the invention may be carried out using traditional sizing/desizing equipment, e.g., pad systems, J-boxes, jets, jiggers, etc. In general, no additional process equipment is needed.

According to the invention, simultaneous desizing and demineralisation are carried out by incubating sized fabric in an aqueous treating solution having a pH in the range between 1 and 5 which aqueous treating solution comprises an alpha-amylase. In a preferred embodiment the pH during incubation is in the range between 1 and 4, especially between pH 2 and 4. The optimal period is dependent upon the type of processing regime and the temperature and can vary from about 15 minutes to several days, e.g., 48 hours. A process of the invention is preferably carried out at a temperature in the range from 5 to 90° C., in particular 20 to 90° C. dependent on the processing regime.

The processing regime can be either batch or continuous with the fabric being contacted by the aqueous treating stream in open width or rope form.

Continuous operations may use a saturator whereby an approximate equal weight of treating solution per weight of fabric is applied to the fabric, followed by a heated dwell chamber where the chemical reaction takes place. A washing section then prepares the fabric for the next processing step. In order to ensure a high whiteness or a good wettability and resulting dyeability, the desizing enzyme(s) and other agents must be thoroughly removed.

Batch processes may take place in one bath (treating solution) whereby the fabric is contacted with, e.g., approximately 8-15 times its weight of aqueous treating solution. After an incubation period, the aqueous treating solution is drained, the fabric is rinsed, and the next processing step is initiated. Discontinuous PB-processes (i.e., pad-batch processes) involves a saturator whereby an approximate equal weight of aqueous treating solution per weight of fabric is applied to the fabric, followed by a dwell period, which in the case of CPB-process (i.e., cold pad-batch process) might be one or more days. For instance, a CPB-process may be carried out at between 20-40° C. for 8-24 hours or more at a pH in the range between 1 and 5, preferably at a pH in the range between around 1 and 4, especially between pH 2 and 4. Further, a PB-process may be carried out at between 40-90° C. for 1-6 hours at a pH in the range between around 1 and 5, preferably between around pH 1 and 4, especially between pH 2 and 4.

In some aspects, the polypeptide of the present invention may also be useful in baking, detergent and pulp and paper production.

Signal Peptide

The present invention also relates to nucleic acid constructs comprising a gene encoding a protein, wherein the gene is operably linked to one or both of a first nucleotide sequence encoding a signal peptide comprising or consisting of amino acids 1 to 18 of SEQ ID NO: 2, wherein the gene is foreign to the first and second nucleotide sequences.

In a preferred aspect, the first nucleotide sequence comprises or consists of nucleotides 1 to 54 of SEQ ID NO: 1.

The present invention also relates to recombinant expression vectors and recombinant host cells comprising such nucleic acid constructs.

The present invention also relates to methods of producing a protein comprising (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides that comprise a combination of partial or complete polypeptide sequences obtained from at least two different proteins wherein one or more (several) may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

EXAMPLES

Chemicals used as buffers and substrates were commercial products of at least reagent grade.

Methods:

Glucoamylase Activity (AGU)

Glucoamylase activity may be measured in AmyloGlucosidase Units (AGU). The AGU is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
| --- | --- |
| Substrate: | maltose 23.2 mM |
| Buffer: | acetate 0.1M |
| Ph: | 4.30 ± 0.05 |
| Incubation temperature: | 37° C. ± 1 |
| Reaction time: | 5 minutes |
| Enzyme working range: | 0.5-4.0 AGU/mL |
| Color reaction: | |
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

Desizing (Tegewa Method)

The starch size residue is determined visually by comparing an iodine stained fabric swatch to a standard set of photos with 1-9 scale where 1 is dark blue and 9 has no color stain. The iodine stain solution is made by dissolving 10 g KI in 10 ml water, add 0.635 g $I_2$, and 200 mL ethanol in deionized water to make total 1 L solution. A fabric sample is cut and immersed in the iodine solution for 60 seconds and rinsed in deionized water for about 5 seconds. The fabric sample is rated by at least two professionals after excess water in the sample is pressed out. An average number is given. Method and standard scales obtainable from Verband TEGEWA, Karlstrasse 21, Frankfurt a.M., Germany.

Metal Ion Detection

The concentration of Fe and Mn on the swatches was detected by Inductively Coupled Plasma Atomic Emission Spectroscopy (ICP-AES) (PerkinElmer, USA). The results are average value of 4 measurements.

Example 1

The Production of the Alpha-amylase of the Present Invention Cloned from *Subulispora* Strain Material and Method Materials:

Oligonucleotide primers for polymerase chain reaction (PCR) were custom-made by Shanghai Sangon Biological Engineering & Technology and Service Co. Ltd. The RNeasy Mini Kit and the DNeasy Plant Mini Kit were purchased from Qiagen Company. The pGEM-T Vector System I and Wizard Plus Minipreps DNA Purification System were purchased from Promega company. The 3' Rapid Amplification of cDNA End System, the Platinum Taq HIFI Taq DNA polymerase and *E. coli.* DH10B competent cell were purchased from Invitrogen Company. DNA Walking SpeedUp Kit was purchased from Seegene. The DNA Marker: 100 bp DNA ladder was purchased from New England Biolab.

Fungal Strain:

*Subulispora* sp. strain was isolated from China.

Fermentation and Mycelium Harvesting:

4-6 agar plugs with fully grown fungal cultures on the PDA plates were used to inoculate one shake flask with FG4 medium (1.5% maltose, 3% soy meal, 0.5% Bacto Peptone, 0.2% PLURONIC L61 by weight) and incubated under room temperature, 160 rpm for 96 hours. Mycelium was harvested by filtering against miracloth and squeezing dry. It was quickly frozen in liquid $N_2$ and stored at −80° C.

Gene Cloning:

1. Primer Design

Two degenerate primers were designed based on conserved region of known amylase sequences.

```
AmyD1:
5'-g(gc)n tac ca(tc) ggn tac tgg-3'   (SEQ ID NO: 3)

AmyD2.5R:
5'-gtc gtg gtt ctc ga(tg)(ag) aa-3'   (SEQ ID NO: 4)
```

2. Genomic DNA and Total RNA Preparation and cDNA Synthesis

The genomic DNA was extracted by using the DNeasy Plant Mini Kit. The total RNA was isolated by using The RNeasy Mini Kit. The cDNA was synthesized by following the instruction of 3' Rapid Amplification of cDNA End System (3' RACE).

3. PCR Amplification:

3.1 Partial Gene Cloning

The PCR was performed by using AmyD1 and AmyD2.5R as primer pair and the genomic DNA as template. The detailed procedure is:

| 10x PCR buffer | 5 ul |
|---|---|
| 25 mM MgCl$_2$ | 2 ul |
| 10 mM dNTP | 1 ul |
| 100 uM AmyD1 | 1 ul |
| 100 uM AmyD2.5R | 1 ul |
| Genomic DNA | 2 ul |
| Taq Hifi | 0.5 ul |
| H2O | 37.5 ul |

PCR program: 94° C. for 2 mins; 30 cycles of 94° C. for 40 secs, 50° C. for 40 secs and 72° C. for 1 min, final extension at 72° C. for 10 mins.

A specific amplification at ~800 base pairs was recovered from gel and directly sequenced. It was confirmed to be an amylase. Based on this partial sequence, new primers were designed for 5' end cloning:

```
Amy-SPR1
5'-TGGAGGTCAAGTTGCTGTAGTC-3'        (SEQ ID NO: 5)

Amy-SPR2
5'-GCAACTGTAGACGATTCGGACTGTA-3'     (SEQ ID NO: 6)
```

3.2 5' End Cloning

For 5' end cloning, the DW-ACP (DNA Walking-Annealing Control Primer) PCR was performed with the DNA Waking SpeedUp kit. The first PCR was performed with primer pair Amy-SPR1 with 4 DW-ACP primers: DW-ACP1, 2, 3, 4 (supplied by DNA Waking SpeedUp kit) separately. The genomic DNA was used as template.

```
DW-ACP1:  5'-ACP-AGGTC-3'
DW-ACP2:  5'-ACP-TGGTC-3'
DW-ACP3:  5'-ACP-GGGTC-3'
DW-ACP4:  5'-ACP-CGGTC-3'
```

The PCR program is: 1 cycle of 94° C. for 5 mins, 42° C. for 1 min, 72° C. for 3 mins; 35 cycles of 94° C. for 40 secs, 50° C. for 40 secs and 72° C. for 3 minutes; final extension at 72° C. for 7 mins.

Nested PCR was performed with primer pair Amy-SPR2 and the Universal primer (5'-TCA CAG AAG TAT GCC AAG CGA-3', supplied by DNA Waking SpeedUp kit), and 100× diluted 1st PCR solution obtained above as template. The PCR program is 94° C. for 3 mins, 10 cycles of 94° C. for 40 secs, 65° C. for 40 secs (decrease 1° C. per cycle) and 72° C. for 1 minute; 29 cycles of 94° C. for 40 secs, 55° C. for 40 secs and 72° C. for 1 minute; final extension at 72° C. for 10 mins.

A specific fragment at ~800 base pairs was obtained from the nested PCR by Amy-SPR2 and universal primer as primer pairs and 1st PCR solution (by DW-ACP1 and Amy3161SPR1) as template. It was identified as the 5' end of an amylase. Then the 5' end primers were designed for full length cloning:

```
Amy-FLF2:
5'-ATGCGGGCGAACGGCATTTTA-3'         (SEQ ID NO: 7)
```

3.3 Full Length Cloning from cDNA

Finally, the full length gene was cloned by PCR with Amy-FLF2 and AUAP (supplied by 3' Rapid Amplification of cDNA End System) by using HIFI Taq DNA polymerase. The detailed procedure is:

| 10x PCR buffer | 5 ul |
|---|---|
| 25 mM MgCl$_2$ | 2 ul |
| 10 mM dNTP | 1 ul |
| 10 uM Amy3161FLF2 | 1 ul |
| 10 uM AUAP | 1 ul |
| The first strand cDNA | 2 ul |
| Taq Hifi | 0.5 ul |
| H$_2$O | 37.5 ul |

The PCR program was: 94° C., 3 mins; 10 cycles of 94° C. for 40 secs, 60° C. for 40 secs with 1° C. decrease per cycle, 68° C. for 2 min; 25 cycles of 94° C. for 40 secs, 50° C. for 40 secs, 72° C. for 2 min; final extension at 72° C. for 10 mins. A specific fragment at 2 kb was amplified. It was identified as an amylase.

The obtained PCR fragment was cloned into pGEM-T vector and transformed into *E. coli* DH10B. The positive clone was sequencing confirmed and deposited in DSMZ as DSM19686 (DSMZ-Deutsche Sammlung von Mikroorganismen and Zellkulturen GmbH, Mascheroder Weg 1b, D-38124 Braunschweig, Germany) on Sep. 19, 2007. Sequence analysis of the cDNA clone showed that the sequence contains a coding region of 1845 nucleotides in SEQ ID NO: 1. The deduced amino acid sequence of this gene with a putative signal peptide of 18 amino acids is shown in SEQ ID NO: 2.

Example 2

The Expression of the Alpha-amylase of the Present Invention

A standard PCR reaction was run using the plasmid in the deposited strain DSM19686 as template and Amy-IF_N-Bam and Amy-IF_C-Eco as primers:

```
Amy-IF_N-Bam:
                                    (SEQ ID NO: 8)
ATTATTCGAAGGATCCACCATGCGGGCGAACGGCAT

Amy-IF_C-Eco:
                                    (SEQ ID NO: 9)
GATGGTGATGGAATTCCGTCTGCCACGTGTCAGACACG
```

The PCR fragment obtained above was digested with BamHI and EcoRI, and ligated into the expression plasmid pLIZGaH (FIG. 1) digested with the same restriction enzymes. The resulting plasmid was designated as pLIZGaH-AMY.

The plasmid was transformed into *Pichia pastoris* (a commercial available yeast cell) using standard technique (cf. WO 2004/069872). The resulting transformants were screened for amylase expression using blue substrate AZCL-HE-amylose (Megazyme) by microtiter plate assay. The absorbance is measured by BioRad Microplate Reader at 595 nm. For checking of purity and determining the molecular weight of purified amylase, enzyme samples were applied to invitrogen SDS-polyacrylamide gel electrophoresis. The transformant both giving the highest OD595 and the strongest band was chosen for further fermentation and subsequent purification of the amylase.

Example 3

The Purification of the Alpha-amylase of the Present Invention

The pH of culture supernatant from example 2 was adjusted to 7.3 with NaOH, then filtered through a 0.45 um filter. The solution was applied to a 30 ml Ni-sepharose High Performance column (GE Healthcare) equilibrated with 20 mM Tris-HCl containing 0.3 M NaCl at pH7.3. The protein was eluted with a linear imidazole gradient (0-500 mM). Fractions from the column were analyzed for amylase activity.

Fractions with amylase activity were checked by SDS-PAGE and the pure fractions were pooled. The SDS-PAGE showed the molecular weight was about 60 kDa.

Example 4

Characterization of the Alpha-amylase of the Present Invention

The alpha-amylase of SEQ ID NO: 2 as purified in the example was characterized according to the following methods.

Determination of Alpha-amylase Activity

When used according to the present invention the activity of any acid alpha-amylase may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, i.e., acid stable alpha-amylase, an endo-alpha-amylase (1,4-alpha-D-glucan-glucano-hydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

Reaction condition: 10 ul standard or enzyme sample, 70 ul $H_2O$, and 80 ul starch working solution (The final concentration was starch 0.35 g/L, Acetate buffer 50 mM pH 5.0, NaCl 0.1 M, $CaCl_2$ 3 mM) mixed and react for 2 minutes with shaking at 37° C. Add 40 ul Iodine working solution (the final iodine concentration was 0.04 g/L) and react at 37° C. for 1 minute. Reading OD590 (Before reading, shaking 10 seconds).

FUNGAMYL™ (available from Novozymes A/S) is used as standard. The activity of alpha-amylase of SEQ ID NO: 2 of the present invention is 6264 AFAU/g.

AZCL-HE-amylose Assay 5 microliters enzyme sample and 120 microliters 1% AZCL-HE-amylose (Megazyme International Ireland Ltd.) at pH 7 were mixed in a Microtiter plate and place on ice before reaction. The assay was initiated by transferring the Microtiter plate to an Eppendorf thermomixer, which was set to the assay temperature 50° C. Then 70 microliters supernatant was transferred to a new microtiter plate. OD595 was read as a measure of amylase activity. All reaction was done with duplicate and a buffer blind was included in the assay (instead of enzyme).

pH Profile 5 microliters enzyme sample from example 3 and 120 microliters 1% AZCL-HE-amylose in B&R buffer (Britton-Robinson buffer: 0.1 M boric acid, 0.1 M acetic acid, and 0.1 M phosphoric acid) adjusted to pH-values 3.0, 4.0, 5.0, 6.0, 7.0, 8.0, 9.0, 10.0 and 11.0 with HCl or NaOH were mixed in an Microtiter plate and placed on ice before reaction. The assay was initiated by transferring the Microtiter plate to an Eppendorf thermomixer, which was set to the assay temperature 50° C. Then 70 microliters supernatant was transferred to a new microtiter plate. OD595 was read as a measure of amylase activity. All reaction was done with duplicate and a buffer blind was included in the assay (instead of enzyme).

The enzyme appears to have activity in a broad pH-range from pH 3-5. The optimum pH is around 4.

pH Stability 30 ul enzyme from example 3 added into 270 ul buffer (100 mM Na-acetate) at pH 4, incubated at 40° C. for 0, 10, 30, 60 and 120 min, 50 ul taken for reaction at each time point. The enzyme was added into 120 ul buffer at pH 4.5 containing 0.2% AZCL-HE-amylose at 40° C. for 20 min, 70 ul taken for OD595.20% ethanol was added to test pH stability.

The enzyme appears to be stable at acidic condition. It still has around 60% residual activity even after incubation 30 mins at pH 4, 40° C.

Temperature Profile 50 ul enzyme was added into 100 ul buffer (100 mM Tris-HCl) at pH 7, and 20 ul 2% AZCL-HE-amylose were added, incubating for 20 min at 20, 30, 40, 50, 60, 70, and 80° C. Then the sample stored in ice for 10 mins. 70 ul supernatant was taken for OD595.

The enzyme is active in a wide range of temperatures from 20-50° C. and appears to have its optimum temperature around 40° C.

Temperature Stability 50 ul enzyme was incubated at 60° C. for 0, 5, 10, 30, 60 and 120 min, 5 ul taken and put on ice at each time point. Then 120 ul pH 4.5 0.2% AZCL-HE-amylose added at 40° C. for 20 min, 70 ul taken for OD595. However, this enzyme was not stable at this condition.

Example 5

Simultaneous Saccarification and Fermentation (SSF) of Raw Starch

Yeast rehydration was carried out in lab under following condition: About 5.5 g dry yeast Ethanol Red™ (available from Fermentis, Marcq-en-Barceul cedex, France) was added in 100 ml tap water. The yeast solution was then stirred at 100 rpm and incubated at 37° C. in a water bath for 30 min. The yeast is ready for use in the following step of SSF.

Raw starch (granular starch) simultaneously saccharification and fermentation (SSF) tests were evaluated via mini-scale fermentations under anaerobic condition. 410 g of ground yellow dent corn with an average particle size around 0.5 mm (available from POET, SD, USA) was added to 584 g tap water. This mixture was supplemented with 6.0 ml of 1 g/L penicillin and 1 g of urea. The pH of this slurry was adjusted to 4.5. Dry solid (DS) level was determined to be about 35% w/w. Approximately 5 g of this slurry was added to 10 ml tubes. Each tube was dosed with the appropriate amount of the alpha-amylase of the present invention and glucoamylase (AMG) according to Table 1, followed by addition of about 100 microliters yeast solution per 5 g slurry. Actual enzyme dosages were based on the exact weight of corn slurry in each tube. Tubes were incubated at 32° C. Six replicate fermentations of each treatment were run. Fermentation tubes were vortexed by hand at 48 and 70 hours. Three tubes were taken at 48 hours, and 70 hours time point to be analyzed by HPLC.

The HPLC sample preparation consisted of immediately stopping the reaction by addition of 50 microliters 40% $H_2SO_4$ in each 5 g sample, centrifuging at 3000 rpm and at room temperature for 5 minutes, and then filtering through a 0.45 micrometer filter. Samples were stored at 4° C. prior to analysis. Agilent™ 1100 HPLC system coupled with RI detector was used to determine concentrations of ethanol and sugars. The separation column was Aminex HPX-87H ion exclusion column (300 mm×7.8 mm) from BioRad™. The analysis was at 0.6 ml/minute flow rate using 5 mM $H_2SO_4$ as mobile phase and the separation column was kept at 65° C. and RI detector at 55° C.

The amount of ethanol produced is shown in Table 1 below. It is evident that the alpha-amylase in this invention boosts ethanol yield from raw starch in SSF, regardless of time and glucoamylase. For example, after 70 hour SSF of raw starch from ground corn, about 151.9 g/l ethanol (i.e., 19.25% v/v ethanol) was produced when alpha-amylase of the present invention is added in combination with *Trametes cingulata* AMG (AMG1), compared to only 118.3 g/l ethanol when no alpha-amylase was added.

2. 50 mM Acetate buffer (pH 5.0): 2.87 g of Sodium Acetate and 0.9 g of Acetic Acid are dissolved in 1 L of de-ionized water.

The 428R woven cotton fabric was from Test Fabrics and cut to 15 cm*25 cm. 100 ml oxalate buffer at pH 2.5 was added to a beaker, Leophen M was added to a concentration of 1 g/L. The stock solution of alpha-amylase of SEQ ID NO:2 in the present invention was added to the impregnation solution to 219 AFAU/L and mixed well. Fixed 1 swatch of fabric in a pair of forceps and dipped the swatch in the impregnation bath for 60 seconds and padded it with the padder (Mathis Inc, U.S.A.). The wet pick-up was checked to be 100%. Placed the swatch in two layers of plastic bag, pressed out the air and place the bag at room temperature. After 18 hours, the sample was removed from the plastic bag. Fixed the sample in the forceps and dipped them in a water bath at 90° C. for 30 seconds and squeeze with padder. Repeated the dipping and squeezing twice. Rinsed the fabric in cold tap water for at least 60 s and squeezed off the water by hand. Then dried the fabric in the air and measured TEGEWA and metal ions on the fabric. A control sample was made by following the same procedure but eliminating the amylase from the impregnation solution. Results are given in Table 2. Addition of alpha-amylase of SEQ ID NO: 2 in the present invention improved the removal of starch, proofed by an increased TEGEWA rating. After the desizing treatment, the content of Fe and Mn was found to decrease from 13 ppm to 1.9 ppm and 4.5 ppm to 1.4 ppm, respectively. Concentration of ferrum above 10 ppm has been reported to be harmful for bleaching. Desizing

TABLE 1

Ethanol Yield in One-step Raw Starch to Ethanol SSF Process

| Sample No | AMG 1* (AGU/gDS) | AMG 2** (AGU/gDS) | AMG 3*** (AGU/gDS) | Alpha-amylase^ (AFAU/gDS) | Ethanol (g/l) 48 hours | Ethanol (g/l) 70 hours |
|---|---|---|---|---|---|---|
| 1 | 0.504 | | | | 95.6 | 118.3 |
| 2 | | 0.713 | | | 114.1 | 141.0 |
| 3 | | | 1.84 | | 89.9 | 116.4 |
| 4 | | | | 0.157 | 35.8 | 46.4 |
| 5 | 0.504 | | | 0.157 | 134.8 | 151.9 |
| 6 | | 0.713 | | 0.157 | 133.7 | 152.0 |
| 7 | | | 1.84 | 0.157 | 125.3 | 148.2 |

Note:
AMG 1* is a glucoamylase derived from *Trametes cingulata* disclosed in SEQ ID NO: 2 in WO 2006/069289.
AMG 2** is a glucoamylase derived from *Aspergillus niger* (SWISSPROT P04064, Carlsberg Res. Commun. 48: 529-544(1983)).
AMG 3*** is a glucoamylase derived from *Talaromyces emersonii*, disclosed in WO9928448, SEQ ID NO: 7.
Alpha-amylase^ is the alpha-amylase of SEQ ID NO: 2 in the present invention.

Example 6

Cold Pad-batch Simultaneous Desizing and Demineralization

Materials:
Fabric
  428R woven cotton (Test fabrics, Inc.)
Chemical
  Surfactant: Leophen M (BASF)
Buffer
1. Oxalate buffer (pH 2.5): 2.7 g of Oxalic Acid Dihydrate is dissolved in 800 ml de-ionized water. The pH is adjusted to 2.50 with 2N NaOH. Fill up to 1 L with de-ionized water.

at acidic pH enables the removal of starch size and heavy metals in a single step, by which the process efficiency will be improved and utilities will be saved greatly.

TABLE 2

Desizing and demineralization of cotton woven fabric with alpha-amylase at pH 2.5

| | TEGEWA | Fe, ppm | Mn, ppm |
|---|---|---|---|
| Raw fabric | 1.0 | 13 | 4.5 |
| Buffer treated fabric | 1.0 | 1.9 | 1.4 |
| Enzyme treated fabric | 2.8 | Not available | Not available |

Example 7

Pad-batch Desizing with Alpha-amylase

The same fabric in Example 6 was used in desizing at 60° C. 100 ml acetate buffer at pH 5 was added to a beaker, Leophen M was added to a concentration of 1 g/L. The stock solution of amylase of SEQ ID NO: 2 in the present invention was added to the impregnation solution to 219 AFAU/L and mixed well. The swatch was padded with the impregnation solution at 100% wet pick-up, then incubated at 60° C. for 4 hours and rinsed by following the same procedure as in Example 6. The TEGEWA rating at 4.5 on the enzyme treated fabric clearly indicated the removal of starch while the buffer treated fabric was only scored at 1.0.

Deposit of Biological Material

The following biological material has been deposited under the terms of the Budapest Treaty with the DSMZ-Deutsche Sammlung von Mikroorganismen and Zellkulturen GmbH (DSM), Mascheroder Weg 1 B, D-38124 Braunschweig, Germany, and given the following accession number:

| Deposit | Accession Number | Date of Deposit |
| --- | --- | --- |
| *Escherichia coli* | DSM19686 | Sep. 19, 2007 |

The strain has been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. An isolated polypeptide having alpha-amylase activity, which has at least 95% identity to the mature polypeptide of SEQ ID NO: 2.

2. The polypeptide of claim 1, which has at least 97% identity to the mature polypeptide of SEQ ID NO: 2.

3. The polypeptide of claim 1, comprising or consisting of the mature polypeptide of amino acid 19-615 of SEQ ID NO: 2.

4. The polypeptide of claim 1, which is a fragment of the sequence of amino acids 19-615 of SEQ ID NO: 2, wherein the fragment has one or more amino acids deleted from the amino and/or carboxyl terminus of the sequence of amino acids 19-615 of SEQ ID NO: 2 and has alpha-amylase activity.

5. The polypeptide of claim 1, which is encoded by a polynucleotide that hybridizes under medium stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii), wherein medium stringency conditions are defined as prehybridization and hybridization at 42° C. in 5×SSPE, 0.3% SDS, 200 micrograms/ml sheared and denatured salmon sperm DNA, and 35% formamide following standard Southern blotting procedures for 12 to 24 hours optimally, and washing three times each for 15 minutes using 2×SSC, 0.2% SDS at 55° C.

6. A composition comprising the polypeptide of claim 1 and a glucoamylase.

7. A process for saccharifying starch, comprising treating a starch with a polypeptide of claim 1 to produce saccharified starch.

8. The process of claim 7, further comprising converting the saccharified starch into a syrup containing dextrose and/or maltose.

9. The process of claim 7, wherein the starch is gelatinized or granular starch.

10. The process of claim 7, further comprising fermenting the saccharified starch with a fermenting organism to produce a fermentation product.

11. A process of producing ethanol, comprising:
    (a) saccharifying a starch containing material with glucoamylase and a polypeptide of claim 1; and
    (b) fermenting the material obtained in step (a) in the presence of a fermenting organism to produce ethanol.

12. The process of claim 11, further comprising recovering the ethanol.

13. The process of claim 11, wherein the starch is gelatinized or granular starch.

14. The process of claim 11, wherein the saccharification and fermentation is carried out as a simultaneous saccharification and fermentation process.

15. A process for desizing of a sized fabric containing starch or starch derivatives during manufacture of a fabric, comprising incubating said sized fabric in an aqueous treating solution having a pH in the range between 1 and 5 which comprises a polypeptide of claim 1.

* * * * *